(12) United States Patent
Cronenberg et al.

(10) Patent No.: US 8,500,682 B2
(45) Date of Patent: Aug. 6, 2013

(54) MEDICAL INJECTOR WITH POST-AUTORECONSTITUTION DOSE SETTING AND AUTOPLUNGER DRIVE

(75) Inventors: Richard A. Cronenberg, Mahwah, NJ (US); Asif Fayyaz, Paramus, NJ (US); Atul Patel, Wilkes-Barre, PA (US); Lionel Vedrine, Palo Alto, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/119,266

(22) PCT Filed: Sep. 18, 2009

(86) PCT No.: PCT/US2009/057485
§ 371 (c)(1),
(2), (4) Date: Nov. 1, 2011

(87) PCT Pub. No.: WO2010/033808
PCT Pub. Date: Mar. 25, 2010

(65) Prior Publication Data
US 2012/0041367 A1 Feb. 16, 2012

Related U.S. Application Data

(60) Provisional application No. 61/192,389, filed on Sep. 18, 2008, provisional application No. 61/192,467, filed on Sep. 18, 2008.

(51) Int. Cl.
*A61M 37/00* (2006.01)
*A61M 5/20* (2006.01)

(52) U.S. Cl.
USPC .......................................... 604/90; 604/135

(58) Field of Classification Search
USPC ............................... 604/82–92, 131, 134–137
See application file for complete search history.

(56) References Cited

U.S. PATENT DOCUMENTS

| | | | | |
|---|---|---|---|---|
| 4,689,042 | A | * | 8/1987 | Sarnoff et al. .................. 604/89 |
| 4,755,169 | A | * | 7/1988 | Sarnoff et al. ................ 604/511 |
| 5,584,815 | A | | 12/1996 | Pawelka et al. |
| 6,096,002 | A | | 8/2000 | Landau |
| 6,203,530 | B1 | | 3/2001 | Stewart, Sr. |
| 6,793,646 | B1 | | 9/2004 | Giambattista et al. |
| 7,407,494 | B2 | | 8/2008 | Bostrom et al. |

(Continued)

FOREIGN PATENT DOCUMENTS

| | | |
|---|---|---|
| FR | 2 741 810 A1 | 6/1997 |
| WO | 2007131013 A1 | 11/2007 |

*Primary Examiner* — Theodore Stigell
*Assistant Examiner* — Nathan R Price
(74) *Attorney, Agent, or Firm* — Hoffmann & Baron, LLP

(57) ABSTRACT

A medical injector is provided herein having a body; a reservoir containing first and second mixable component; a stopper; a plunger; a spring disposed to advance the plunger; a first releasable retainer for releasably retaining the plunger in a first state against force of the spring; a first trigger for causing the first releasable retainer to release the plunger; a second releasable retainer for releasably retaining the plunger in a second state against force of the spring; and, a second trigger for causing the second releasable retainer to release the plunger. The spring causes the plunger to advance so that the stopper traverses at least a predetermined extent of advancement thereby causing mixing of the first and second mixable components. Advantageously, with the subject invention, a medical injector is provided which allows for autoreconstitution with subsequent dose setting and autoplunger activation being activated by separate triggers.

3 Claims, 6 Drawing Sheets

U.S. PATENT DOCUMENTS

| | | | |
|---|---|---|---|
| 8,092,420 B2 * | 1/2012 | Bendek et al. | 604/89 |
| 2004/0133163 A1 | 7/2004 | Schiffmann | |
| 2006/0178630 A1 * | 8/2006 | Bostrom et al. | 604/135 |
| 2007/0142769 A1 | 6/2007 | Griffiths et al. | |

* cited by examiner

MEDICAL INJECTOR WITH POST-AUTORECONSTITUTION DOSE SETTING AND AUTOPLUNGER DRIVE

FIELD OF THE INVENTION

This invention relates to medical injectors with automatically driven plungers and, more particularly, to medical injectors with automatically driven plungers which permit dose setting.

BACKGROUND OF THE INVENTION

Certain drugs or medicaments (those terms being used interchangeably herein) are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other dry or powder form that require reconstitution.

In addition, drugs may be provided as multipart systems which require mixing prior to administration. For example, one or more liquid (e.g., flowable (slurry or liquid)) components, and/or dry (e.g., powdered or granular) components may be provided in a drug container or delivery device which require mixing prior to administration. The components can be mixed and used to form various administratable drugs, such as insulin.

Prior art devices have been developed that provide a wet component (e.g., liquid) and a dry component (e.g., powder) in separate chambers of a common container with the container being configured to permit the flow of the wet component to the dry component to cause mixing thereof in preparing an administratable solution for injection. U.S. Pat. No. 4,874,381 to Vetter is directed to an injector having a barrel configured for mixing, while U.S. Pat. No. 4,968,299 to Ahlstrand et al. is directed to a drug cartridge having a barrel configured for mixing. Both Vetter et al. and Ahlstrand et al. disclose typical configurations for mixing where a bypass channel is formed in the barrel of the device. As such, the device must be specifically configured for mixing.

Manual force may be applied to a reconstitution device to cause the mixing of the multiple components. In addition, autoreconstitution devices have been developed in the prior art which provide a trigger-activated automated reconstitution. U.S. Pat. No. 6,793,646 to Giambattista et al. is an example of an autoreconstitution device.

It is noted that autoinjectors are known in the prior art which may also cause autoreconstitution. Autoinjectors, however, are trigger-activated devices which not only cause autoreconstitution, but will also cause a needle to pierce a patient's skin with subsequent automated plunger drive causing fluid administration. Autoinjectors typically do not have dose settings. In addition, the needle is pre-mounted to the device. Examples of this type of device may be found in U.S. Published Patent Application No. 2004/0133163 to Schiffmann and in U.S. Published Patent Application No. 2007/0142769 to Griffiths et al.

U.S. Pat. No. 7,407,494 to Bostrom et al. discloses an autoreconstitution device which permits dose setting after reconstitution and subsequent activation of an autoplunger drive which causes automatic plunger actuation resulting in dose administration. The Bostrom et al. device, thus, requires two activations: a first activation to trigger the autoreconstitution; and, a second activation to trigger the autoplunger drive. Bostrom et al. provides a single activator button for both actions. Failure or improper operation during autoreconstitution could possibly prevent subsequent injection even if reconstitution was successfully performed.

SUMMARY OF THE INVENTION

A medical injector is provided herein having a body; a reservoir containing first and second mixable components, a stopper associated with the reservoir, a predetermined extent of advancement of the stopper causing mixing of the first and second mixable components; a displaceable plunger disposed in the body; a spring disposed to advance the plunger; a first releasable retainer for releasably retaining the plunger in a first state against force of the spring; a first trigger for causing the first releasable retainer to release the plunger; a second releasable retainer for releasably retaining the plunger in a second state against force of the spring; and, a second trigger for causing the second releasable retainer to release the plunger. The spring causes the plunger to advance from the first state to the second state. The plunger engages the stopper during the advancement from the first state to the second state so that the stopper traverses at least the predetermined extent of advancement thereby causing mixing of the first and second mixable components. Advantageously, with the subject invention, a medical injector is provided which allows for autoreconstitution with subsequent dose setting and autoplunger activations, the autoreconstitution and the autoplunger activations being activated by separate triggers.

These and other features of the invention will be better understood through a study of the following detailed description and accompanying drawings.

DETAILED DESCRIPTION OF THE INVENTION

Figure 1:
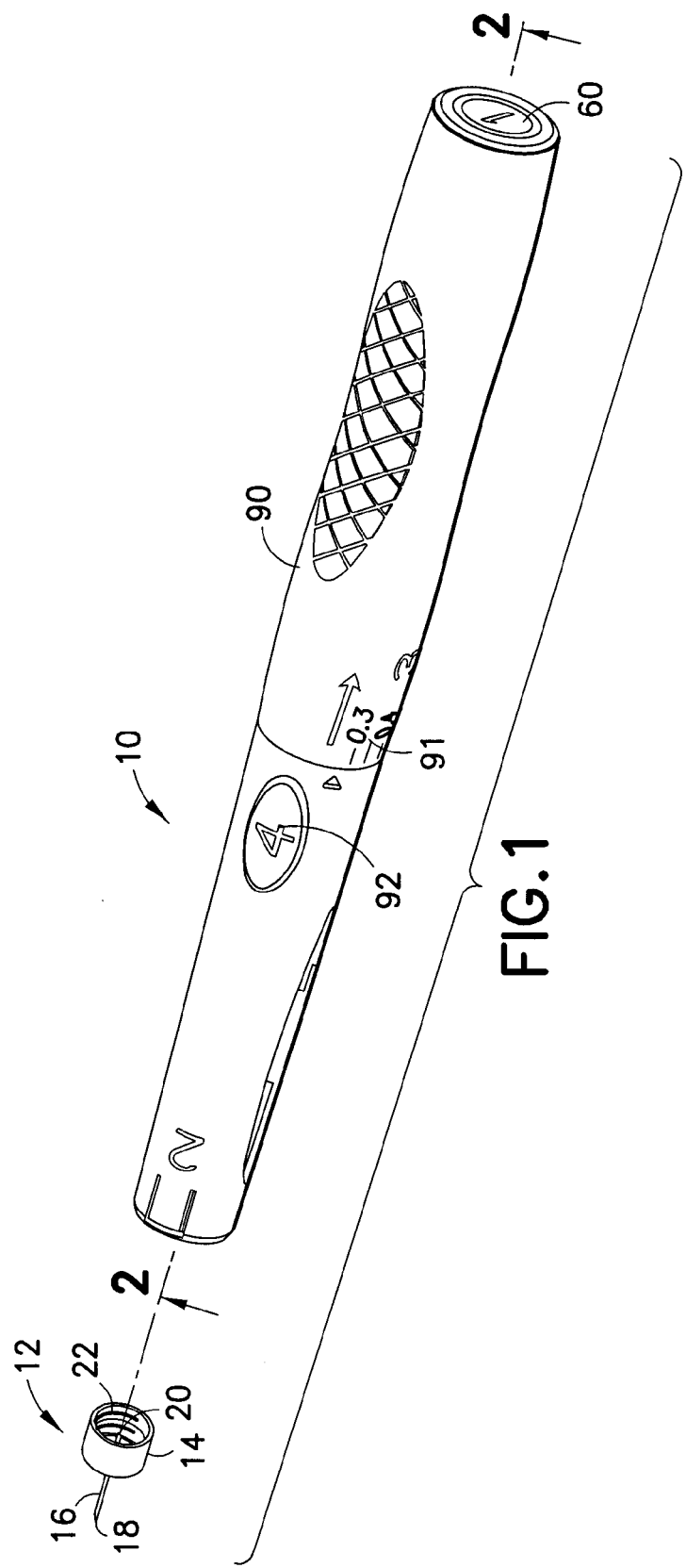
FIG. 1 is a perspective view of a medical injector formed in accordance with the subject invention.

With reference to the Figures, the subject invention provides a medical injector 10 which allows for dose setting after autoreconstitution and prior to autoplunger drive. In particular, the medical injector 10 is configured to permit mounting of a needle 12 thereto. The medical injector 10 may be in the form of any medical injector, such as a syringe or pen injector, which is capable of reconstituting mixable components accommodated therein into an administrable liquid. The medical injector 10 may be a single- or multiple-dose device.

The needle 12 may be in any form. Preferably, the needle 12 includes a hub 14 to which is affixed a needle cannula 16. Distal end 18 of the needle cannula 16 is formed for insertion into a patient, while proximal end 20 may optimally be sharpened. The hub 14 may be formed with mounting features 22, such as threads, for mounting onto the medical injector 10, as described below.

As used herein, the term "distal", and derivatives thereof, shall refer to a direction toward a patient during use, while the term "proximal" and derivatives thereof, shall refer to a direction away from a patient during use.

The medical injector 10 includes a body 24 which may be formed of one or more components. The medical injector 10 also includes a needle mounting surface 26 having features 28 for mounting the needle 12 thereto. The features 28 may be of any known type for mounting the needle 12 including features for creating a cooperating mechanical lock with the needle 12, particularly for cooperating with the mounting features 22, such as threads, bayonet lock members, detents, grooves, and so forth, and/or frictional engagement with the hub 14, such as through a tapered Luer configuration.

Figure 2:
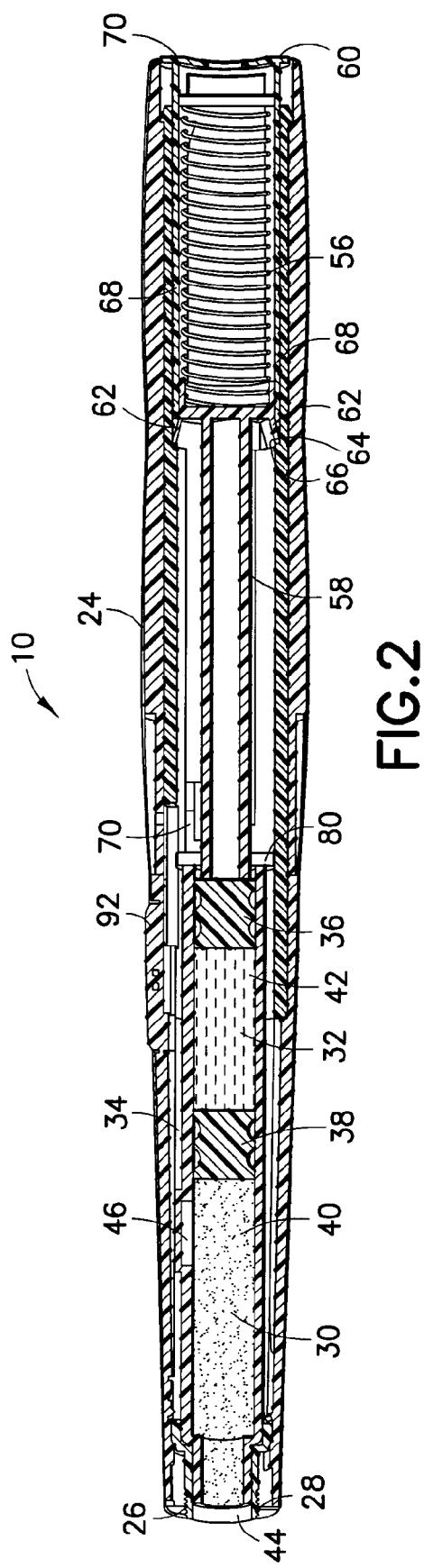
FIG. 2 is a cross-sectional view taken along line 2-2 of FIG. 1.

The medical injector 10 is an autoreconstitution device which, as shown in FIG. 2, includes at least first and second mixable components 30, 32 in an initial state. A reservoir 34 is disposed in the body 24 for accommodating the first and second mixable components 30, 32. At least one stopper 36 is associated with the reservoir 34 configured such that distal advancement of the stopper 36 over a predetermined distance shall cause mixing of the first and second mixable components 30, 32. Any known arrangement for allowing such mixing may be utilized. By way of non-limiting example, the first and second mixable components 30, 32 may be separated by a secondary stopper 38. The secondary stopper 38 divides the reservoir 34 into first and second chambers 40, 42, respectively, accommodating the first and second mixable components 30, 32. A septum 44 seals off the distal end of the first chamber 40, while the stopper 36 is positioned to seal off the proximal end of the second chamber 42. Preferably, if a dry component is used as one of the mixable components, the dry mixable component is located in the first chamber 40.

One or more by-pass channels 46 are formed in the wall of the reservoir 34. In an initial state, as shown in FIG. 2, the secondary stopper 38 is located at least partially proximally of the by-pass channels 46 so as to define a seal between the first and second chambers 40, 42 and to define a seal between the second chamber 42 and the by-pass channels 46. With distal advancement of the stopper 36, and with the second mixable component 32 being wet and generally incompressible, force of movement of the stopper 36 is transmitted to the secondary stopper 38 through the second mixable component 32. With sufficient distal movement of the secondary stopper 38, the second chamber 42 comes into communication with the by-pass channels 46, thus allowing the second mixable component 30 to be urged into the first chamber 40 with further distal movement of the stopper 36. With reference to FIG. 2, with sufficient distal advancement of the stopper 36, the second chamber 42 is collapsed with none or substantially none of the second mixable component 32 remaining therein. In addition, the secondary stopper 38 is located so as to define a seal between the first chamber 40 and the by-pass channels 46. The first and second mixable components 30, 32 are mixed within the first chamber 40, such as through agitation of the medical injector 10, so as to produce an injectable solution, ready for injection.

As will be recognized by those skilled in the art, other arrangements for permitting reconstitution may be utilized. In addition, more than two-part systems, such as three-part, and so forth, systems may be utilized. Active medical ingredients may be included in one or both of the first and second mixable components 30, 32. The first mixable component 30 may be dry (e.g., a powder or granular substance) and/or a liquid (e.g., flowable (slurry or liquid)). As mentioned above, the second mixable component 32 is preferably only a wet flowable component such as a liquid or slurry.

It is preferred that movement of the stopper 36 be automated to achieve autoreconstitution. Various trigger-activated autoreconstitution configurations are known in the prior art, such as that disclosed in U.S. Pat. No. 6,793,646 to Giambattista et al., which is incorporated by reference herein in its entirety. As shown in FIG. 2, a spring 56 may be provided to cause plunger 58 to drive forward. The plunger 58 acts against the stopper 36 in achieving autoreconstitution of the first and second mixable components 30, 32, as described above. The spring 56 may act, via the plunger 58, to distally drive the stopper 36 from the initial first position of FIG. 2. The spring 56 may be of any type, including coil or compression spring. Other types of biasing elements may be also utilized.

The plunger 58 is retained in the first position of FIG. 2 by any known manner of releasable retaining mechanism. A trigger may be provided to release the retaining mechanism to cause autoreconstitution and advancement of the plunger 58. As indicated above, U.S. Pat. No. 6,793,646 to Giambatista et al. discloses an injector with trigger-activated autoreconstitution where autoreconstitution is activated by collapsing together two body parts of the injector. The collapsing effect causes release of the plunger and autoreconstitution.

Alternatively, as shown in FIG. 2, a trigger 60 may be slidably disposed in the body 24, and the plunger 58 may include one or more deflectable latch tabs 62. In the initial first state of FIG. 2, the latch tabs 62 have free ends 64 which interferingly engage ledges 66. Interengagement between the latch tabs 66 and the ledges 66 retains the plunger 58 in the first state against force of movement of the spring 56. The trigger 60 includes one or more arms 68 which define a smaller diameter than the latch tabs 62. With sufficient distal advancement of the trigger 60, e.g. being caused by force being applied to proximal end 70 thereof, the arms 68 engage the latch tabs 62 and cause inward deflection thereof. With inward deflection of the latch tabs 62, the spring 56 is free to drive the plunger 58 distally and engage the stopper 36 in causing autoreconstitution.

As will be appreciated by those skilled in the art, other releasable retaining arrangements and triggers may be utilized for retaining the plunger 58 in the initial state and causing release therefrom. For example, a bayonet lock-type releasable retaining arrangement may be utilized which is triggered by rotating one or more portions of the body of the medical injector 10 or rotating an additional component, such as a dose setting knob. Copending applications PCT Application No. PCT/US2009/057439 and PCT Application No. PCT/US2009/057460 disclose releasable retainer arrangements which are triggered by rotation to permit plunger advancement; these applications are incorporated by reference herein in their entireties.

The spring 56 is configured to advance the plunger 58 a predetermined extent of movement. A second releasable retainer 70 is provided to intercept the plunger 58 along its course of advancement in stopping the plunger 58 at a second position. The second position is located so as to prevent the plunger 58 from traversing the entire predetermined extent of movement. In addition, the second position is located so as to permit the plunger 58 to traverse a sufficient distance to drive the stopper 36 a sufficient distance to achieve reconstitution.

Figure 3:
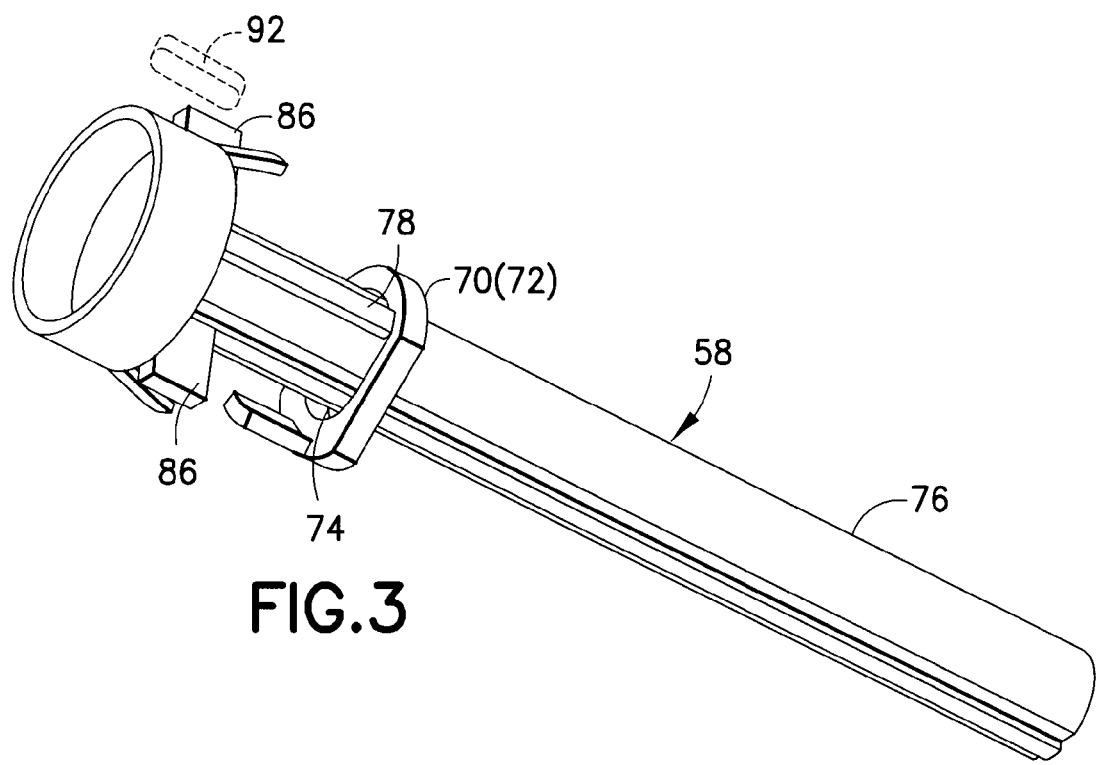
FIGS. 3-6 show a plunger and a second retainer configuration useable with the subject invention.
Figure 4:
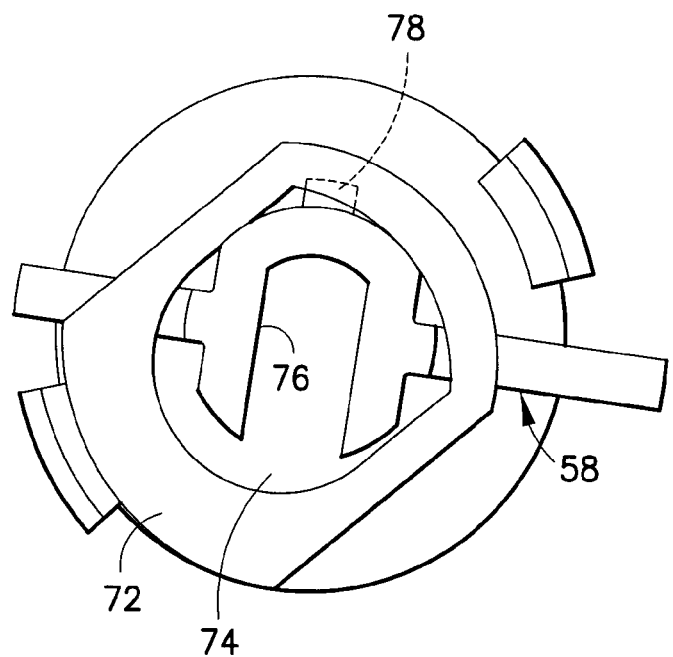
Figure 5:
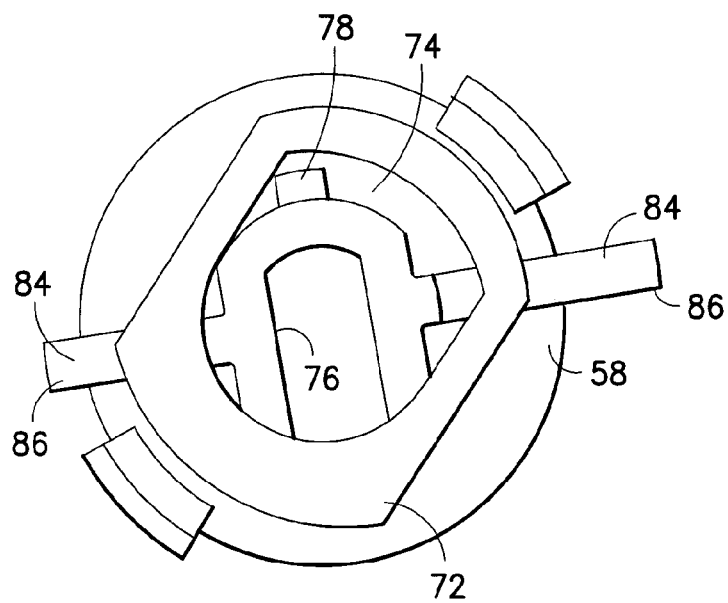

With reference to FIGS. 3-6, the second releasable retainer 70 may include stop block 72 having an opening 74 formed therethrough to permit passage of plunger stem 76 of the plunger 58. The plunger stem 76 is aligned to engage the stopper 36 during use. The opening 74 is formed larger than the cross-section of the plunger stem 76 such that the stop block 72 is axially shiftable relative to the plunger stem 76 between blocking and open states. The stop block 72 is axially shiftable in a direction transverse to the direction of movement of the plunger 58. In the blocking state, as shown in FIGS. 3 and 4, the stop block 72 is formed to interferingly engage stop member 78 formed on the plunger 58 with a portion of the plunger stem 76 passing through the opening 74. In the open state, as shown in FIG. 5, the stop block 72 permits the stop member 78 to pass through the opening 74 with the plunger stem 76.

Figure 6:
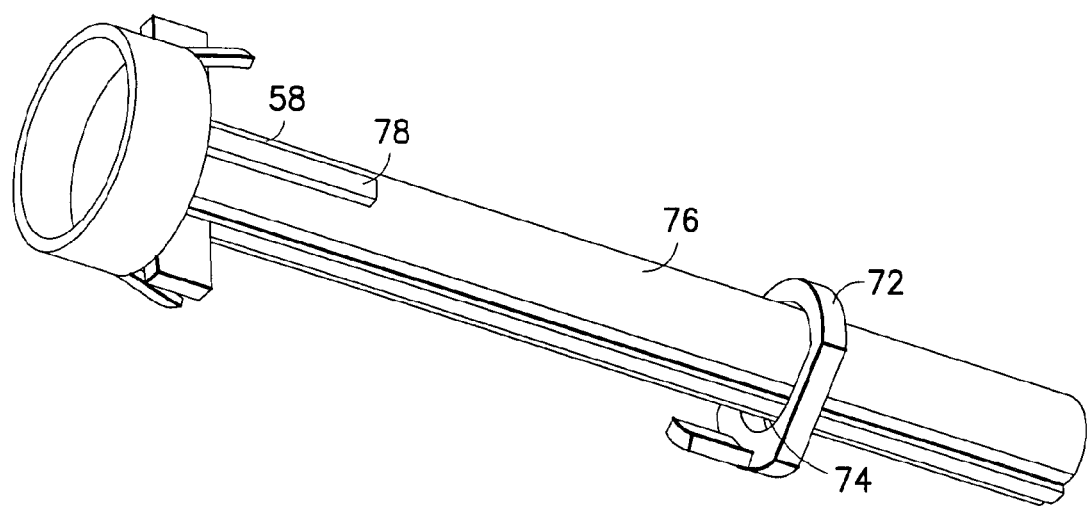

As shown in FIG. 6, in the initial first state, the stop member 78 is axially spaced from the stop block 72. With the plunger 58 being released from the first state, the plunger 58 axially advances with the plunger stem 76 passing through the opening 74. During this movement, the plunger 58 advances the stopper 36 at least a sufficient distance to achieve reconstitution. The stop block 72 is initially in the blocking state. Eventual distal advancement of the plunger 58 causes the stop member 78 to engage the stop block 72, as shown in FIG. 3. The point of engagement between the stop member 78 and the stop block 72 is reached prior to the entire predetermined extent of movement of the plunger 58 for which the spring 56 is configured. Thus, the stop block 72 retains the plunger 58 in this second state against force of movement of the spring 56. Axial shift of the stop block 72 moves the stop block 72 to the open state thus releasing the plunger 58 from the second state.

The stop block 72 is positioned to locate the second state at minimally a distance permitting autoreconstitution to be achieved with the plunger 58 moving from the first state to the second state. Preferably, reconstitution of the first and second mixable components 30, 32 is conducted without the needle 12 mounted to the medical injector 10. As such, the reservoir 34 is not vented during the mixing. In this manner, the mixed components may be maximally compressed under force of the spring 56. With mounting of the needle 12 onto the medical injector 10, the reservoir 34 is vented thus permitting further distal advancement of the plunger 58. This secondary distal advancement may assist in priming a needle for use. It is preferred that autoreconstitution be completed prior to the stop member 78 coming into engagement with the stop block 72. With subsequent mounting of the needle 12 onto the medical injector 10, the reservoir 34 is vented, thus reducing the trapped volume therein. This permits the stopper 36 to be further advanced under force of movement of the spring 56 till trapped gases are purged. It is preferred that the stop member 78 come into engagement with the stop block 72 upon this secondary distal advancement.

Figure 7:
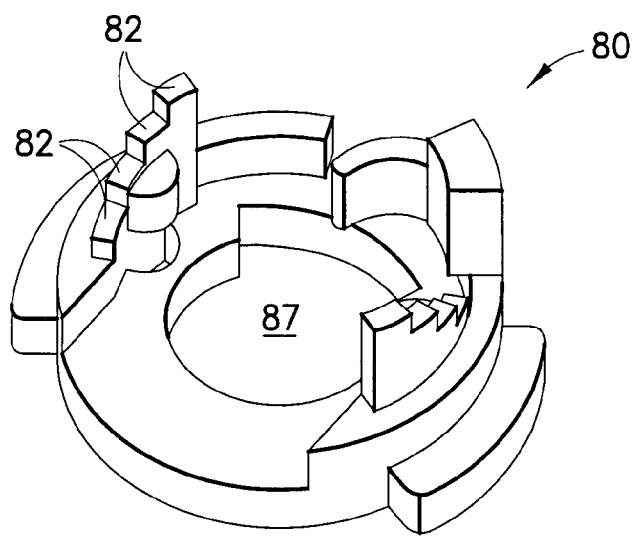
FIGS. 7-8 show a dose ring useable with the subject invention.
Figure 8:
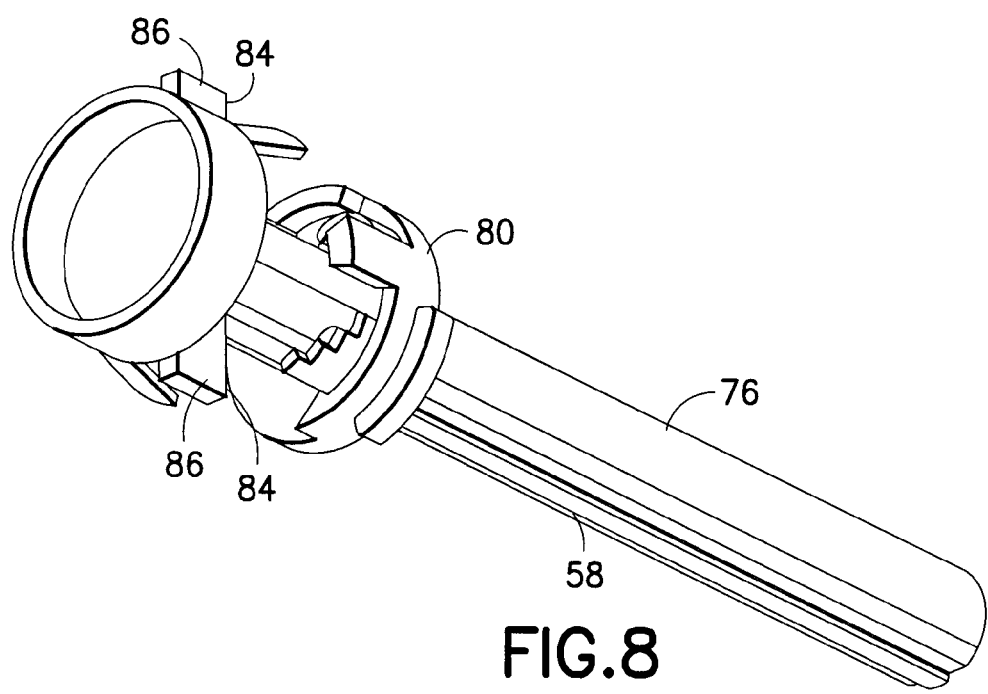

Dose selection may be conducted upon initiation, during or after autoreconstituion. Any configuration for dose selection may be utilized. By way of non-limiting example, and with reference to FIGS. 7 and 8, a dose ring 80 may be provided with a plurality of axially and radially spaced-apart abutment surfaces 82 which represent different dose sizes.

The abutment surfaces 82 are axially alignable with one or more engagement surfaces 84 formed on the plunger 58. One or more tabs 86 may extend from the plunger 58 on which the engagement surfaces 84 may be defined. It is preferred that the tabs 86 be formed to not be passable through the opening 74 of the stop block 72 in either the blocking or open states. The dose ring 80 includes an aperture 87 which permits passage of the plunger stem 76 and the stop member 78 therethrough.

With rotation of the plunger 58, the engagement surfaces 84 may be axially aligned with different of the abutment surfaces 82 thus allowing for dose selection. The engagement surfaces 84 are spaced from the abutment surfaces 82 with the plunger 58 being retained in the second state. The distance between the engagement surfaces 84, located with the plunger 58 being in the second state, and the selected of the abutments surfaces 82 will dictate the stroke length of the plunger 58 during injection and, thus, dictate the dose size. A greater distance will provide a larger dose and, conversely, a smaller distance will provide a smaller dose. Once a dose is set, the needle 12 is inserted into a patient and the stop block 72 is urged from the blocking state to the open state. Consequently, the plunger 58, under force of movement of the spring 56, is advanced distally and, in turn, forces the stopper 36 distally to urge the injectable solution into the patient. Interengagement of the selected abutment surfaces 82 and the engagement surfaces 84 limits the distal movement to produce the selected dose. Movement of the plunger 58 is automated under force of the spring 56 thus producing an autoplunger drive.

Figure 9:
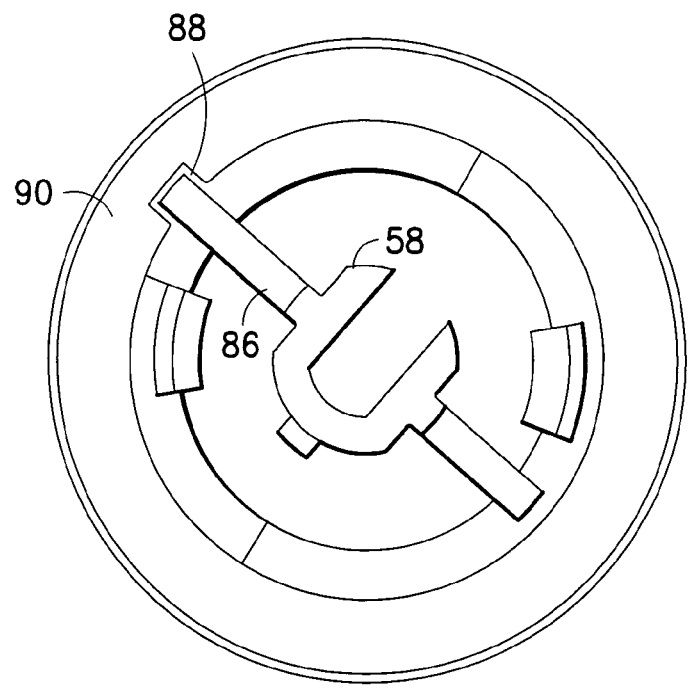
FIG. 9 shows schematically a dose setting configuration useable with the subject invention; and, FIG. 10 shows a configuration of the second retainer and dose ring useable with the subject invention.

As will be appreciated by those skilled in the art, the plunger 58 may be caused to rotate by various configurations. For example, as shown in FIG. 9, one of more of the tabs 86 may be nested in slots 88 formed in an outer body portion 90. With rotation of the outer body portion 90, corresponding rotation of the plunger 58 may be achieved. Indicia 91 (FIG. 1) may be located on the medical injector 10 to assist in dose setting.

The stop block 72 is axially shifted through activation of second trigger 92. Preferably, the second trigger 92 is an inwardly-displaceable button formed on the body 24 and aligned to shift the stop block 72 from the blocking state to the open state with inward displacement. One or more intermediary components may be utilized which transmit force from inward displacement of the second trigger 92 to the stop block 72.

Figure 10:
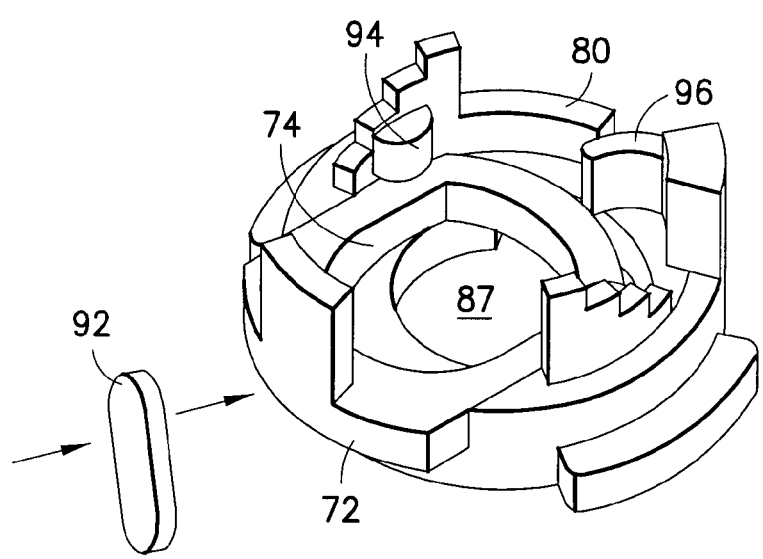

With reference to FIG. 10, it is preferred that the dose ring 80 have retaining clips 94 formed to snap receive the stop block 72 with the opening 74 and the aperture 87 being aligned so as to both permit passage therethrough of the plunger stem 76. The dose ring 80 is formed to permit axial shifting of the stop block 72 between the blocking and open states. A spring arm 96 may extend from the dose ring 80 to bias the stop block 72 to the blocking state. Axial movement of the stop block 72 to the open state is thus against biasing force generated by the spring arm 96.

Dose selection may be conducted at any time prior to release of the plunger 58 from the second state. It is preferred that once a dose is set, axial alignment of the selected abutment surfaces 82 and the engagement surfaces 84 be maintained. Such an arrangement is disclosed in U.S. Pat. No. 6,793,646, which is incorporated by reference herein in its entirety. As shown therein, one or more tabs may be used to engage teeth or channels in a ratchet fashion.

To prevent premature release from the second state, as shown schematically in FIG. 3, one or more of the tabs 86 may be initially radially positioned to block the second trigger 92 from activation prior to dose selection with the plunger 58 being in the second state. In this manner, the second trigger 92 is blocked from inward displacement and, thus, is blocked from shifting the stop block 72 from the blocking state to the open state. With radial adjustment of the tabs 86 in selecting a dose, the second trigger 92 may be freed for activation.

With the subject invention, a medical injector is provided with two distinct triggers for causing autoreconstitution and autoplunger drive, respectively. Advantageously, dose selection is permitted after autoreconstitution and prior to automated plunger drive.

What is claimed is:

1. A medical injector comprising:
   a body;
   a reservoir containing first and second mixable components, a stopper associated with said reservoir, a predetermined extent of advancement of said stopper causing mixing of said first and second mixable components;
   a displaceable plunger disposed in said body;
   a spring disposed to advance said plunger;
   a first releasable retainer for releasably retaining said plunger in a first state against force of said spring;
   a first trigger for causing said first releasable retainer to release said plunger;
   a second releasable retainer for releasably retaining said plunger in a second state against force of said spring; and,
   a second trigger for causing said second releasable retainer to release said plunger,
   wherein, said plunger is advanced from said first state to said second state by said spring, said plunger engaging said stopper during said advancement from said first state to said second state so that said stopper traverses at least said predetermined extent of advancement thereby causing mixing of said first and second mixable components,
   wherein said second retainer includes a stop block axially shiftable between a blocking state and an open state, wherein, in said blocking state, said stop block interferingly engages a stop member formed on said plunger, and, wherein, in said open state, said stop block permits passage therethrough of said stop member, said shifting of said stop block allowing said plunger to be released from said second state.

2. A medical injector as in claim 1, wherein, upon release of said plunger from said second state, said spring advances said plunger a predetermined distance.

3. A medical injector as in claim 2, wherein said predetermined distance is selected prior to said plunger being released from said second state.

* * * * *

UNITED STATES PATENT AND TRADEMARK OFFICE
CERTIFICATE OF CORRECTION

PATENT NO. : 8,500,682 B2  Page 1 of 1
APPLICATION NO. : 13/119266
DATED : August 6, 2013
INVENTOR(S) : Cronenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 87 days.

Signed and Sealed this
Fifteenth Day of September, 2015

Michelle K. Lee
*Director of the United States Patent and Trademark Office*